(12) United States Patent
Falco

(10) Patent No.: US 6,241,042 B1
(45) Date of Patent: Jun. 5, 2001

(54) HEARING PROTECTIVE DEVICE

(75) Inventor: Robert N. Falco, Indianapolis, IN (US)

(73) Assignee: Cabot Safety Intermediate Corporation, Southbridge, MA (US)

( * ) Notice: Subject to any disclaimer, the term of this patent is extended or adjusted under 35 U.S.C. 154(b) by 0 days.

(21) Appl. No.: 09/524,825

(22) Filed: Mar. 14, 2000

Related U.S. Application Data

(60) Provisional application No. 60/124,593, filed on Mar. 16, 1999.

(51) Int. Cl.$^7$ ........................................................ A61B 7/02
(52) U.S. Cl. ........................... 181/135; 181/130; 2/209; D24/106; D29/112; 128/864; 128/867
(58) Field of Search ..................................... 181/135, 134, 181/130, 129; 2/423, 209; 128/864, 865, 867; D24/106, 174, 173; D29/112

(56) References Cited

U.S. PATENT DOCUMENTS

| | | | |
|---|---|---|---|
| D. 375,551 | * | 11/1996 | Esler et al. ............................ D24/106 |
| D. 413,379 | * | 8/1999 | Leight .................................. D24/106 |
| 5,188,123 | | 2/1993 | Gardner, Jr. . |
| 5,449,865 | * | 9/1995 | Desnick et al. ....................... 181/131 |
| 5,792,998 | * | 8/1998 | Gardner, Jr. et al. ................ 181/130 |

FOREIGN PATENT DOCUMENTS

| | | | |
|---|---|---|---|
| 35 36 793 A1 | * | 4/1987 | (DE) . |
| 0 847 736 A1 | | 6/1998 | (EP) . |
| WO 91 05446 | | 4/1991 | (WO) . |
| WO 98 06363 | | 2/1998 | (WO) . |

* cited by examiner

Primary Examiner—Robert E. Nappi
Assistant Examiner—E. San Martin
(74) Attorney, Agent, or Firm—Cantor Colburn LLP

(57) ABSTRACT

An acoustical hearing device is presented, comprising a foam and at least one component which is mechanically bonded to the foam. The mechanical bonding of the component arises during manufacture, wherein the component is placed into a mold cavity as an insert and a foam is formed within the mold so as to allow controlled penetration of the component during foaming. In an exemplary embodiment, the at least one component comprises a stem having a tip at one end, wherein the tip includes at least one opening at least partially extending therethrough. The mechanical bond resulting when the foam extends through the at least one opening.

17 Claims, 3 Drawing Sheets

HEARING PROTECTIVE DEVICE

CROSS-REFERENCE TO RELATED APPLICATIONS

This application claims the benefit of U.S. patent application Ser. No. 60/124,593, filed on Mar. 16, 1999, which is hereby incorporated by referenced in its entirety.

BACKGROUND OF THE INVENTION

1. Field of the Invention

This invention relates generally to acoustical hearing devices. More particularly, this invention relates to hearing protective devices comprising a foam and at least one mechanically bonded component during the manufacturing process.

2. Brief Description of the Prior Art

The use of hearing protection and noise attenuating devices are well known, and various types of devices are available for this purpose. Such devices include, but are not limited to, earmuffs, semi-aural devices, and earplugs. Foam components are well-known for use with these devices, providing both sound attenuation and enhanced comfort for the wearer.

Earplugs are generally preferred for continuous use over longer periods of time. Slow recovery foam earplugs such as those disclosed in U.S. Reissue No. 29,487 are not only comfortable, but have also been shown to deliver high in-field noise protection at all frequencies. U.S. Pat. No. 5,203,352 to Gardner, Jr. also discloses a hearing protective earplug comprising a polymeric foam.

With respect to all three types of devices, the sound-attenuating (acoustical) component has been made both of flexible, rubber-like materials, and of foam. For earplugs and semi-aural devices, the rubber-like materials are advantageous in allowing direct insertion into the wearer's ear, but are sometimes uncomfortable over long periods of use. Foam earplugs and pods provide enhanced comfort, but require "rolling-down" before insertion. In addition, manufacture of foam components requires the presence of a vent in the mold for entrapped gases to escape, which often results in foam overflowing the vent ("flash"). This flash is wasteful, and must be cleaned off the molds after each molding. Cleaning the molds can be a long, tedious procedure which adds significantly to manufacturing time.

A foam earplug or pod with a stem insert can provide both the ease of insertion of rubberlike earplugs, with the comfort of foam earplugs and pods. In fact, a number of patents have been directed to earplugs having tips or flanges with a relatively stiff stem used to insert and remove the earplug. One especially useful earplug, shown in FIG. 1, is described in U.S. Pat. No. 5,188,123 to Gardner, herein incorporated by reference. This earplug 2 comprises a circular or ovoid resilient polymeric foam body 4 having a rounded nose end 6. An elongate stem 8 is axially embedded in main body element 4 and extends rearwardly and axially therefrom. The earplug may be used in a push-in or roll-down insertion mode.

While suitable for certain purposes, this prior art earplug requires an additional manufacturing step to secure the stem in the foam body, i.e., a gluing step. Furthermore, the bond is sometimes not as permanent as is desirable. In addition, if the stem is too hard it may be considered unsafe to the user, the general concern being that potential injury could result should the hearing protector become impacted. On the other hand, if the stem is too soft, it tends to buckle upon insertion, limiting the fit of the earplug and reducing the potential usefulness of the stem.

One attempted solution has been to provide an insertion tool, consisting of a stiff tube that fits over the soft stem. However, the use of an additional part increases the cost of manufacture and may be inconvenient for the user. Another attempted solution has been to use a relatively stiff material, but reduce the diameter of the stem. However, this solution results in decreased comfort for the wearer, apparently due to the increased pressure that results from use of a smaller diameter stem.

Still another exemplary prior art ear plug is disclosed in U.S. Pat. No. 5,799,658 to Falco which is assigned to the assignee hereof, all of the contents of which are incorporated herein by reference. Referring to prior art FIGS. 2 and 3, this prior art earplug or semi-aural device pod 10 comprises a foam 12 mechanically bonded to a porous component 14 having a handle portion 16 and an embedded portion 18 with a tip 20. "Embedded portion" refers here to that part of the porous insert which is surrounded by, and mechanically bonded to, the foam component The earplug may be of any configuration, such as circular or ovoid, with the preferred configuration having a flange 13. During manufacture, porous component 14 is placed in a mold and a foam is formed within the mold such that foam penetrates the embedded portion 18 of porous component 14, thereby forming a mechanical bond between the foam and the porous component.

One problem with the just discussed prior art ear plug is that the sources for porous component 14 are quite limited. For this and other reasons, although the above prior art ear plugs have been satisfactory for their intended purpose, there remains a need for stemmed foam ear plugs that are safe for the wearer, yet convenient and comfortable to use and which does not require a separate gluing step to adhere to the part.

SUMMARY OF THE INVENTION

The above-discussed and other problems and deficiencies of the prior art are overcome or alleviated by the foam hearing protective devices and method of manufacture of the present invention, comprising a foam and at least one component mechanically bonded to the foam during manufacture by controlled penetration of the component by the foam.

In a preferred embodiment of the present invention, an earplug or semi-aural device comprises a foam component mechanically bonded to an insert (stem) having a handle portion and a tip portion comprising an embedded portion. "Embedded portion" refers here to that part of the insert which is surrounded by, and mechanically bonded to, the foam component. During manufacture, the stem insert is placed in a mold and a foam is formed within the mold such that foam extends through at least one opening formed in the stem insert, thereby forming a mechanical bond between the foam and the stem insert.

The above-discussed and other features and advantages of the present invention will be appreciated and understood by those of ordinary skill in the art from the following detailed description and drawings.

BRIEF DESCRIPTION OF THE DRAWINGS

Referring now to the drawings wherein like elements are numbered alike in the several FIGURES.

DESCRIPTION OF THE PREFERRED EMBODIMENT

The acoustical device and method of manufacture of the present invention, specifically called "ear plug stem and foam component" comprises a foam element and at least one stem component mechanically bonded to the foam during manufacture by penetration of at least one stem component by the foam.

Figure 1:
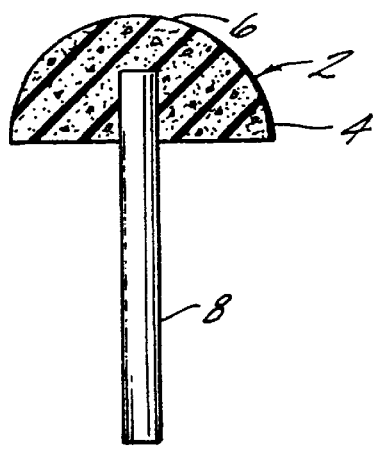
FIG. 1 is a cross-sectional elevation view along the centerline of a prior art ear plug except for the stem portion which is shown in elevation view.

Referring first to prior art FIG. 1, one especially useful ear plug is disclosed in U.S. Pat. No. 5,188,123 to Gardner, herein incorporated by reference. As shown in FIG. 1, ear plug 2 comprises a circular or ovoid resilient polymeric foam body 4 housing a rounded nose 6. An elongated stem 8 is axially embedded in main body element 4 and extends rearwardly and axially therefrom. The ear plug may be used in a push-in or roll down insertion mode. While suitable for certain purposes, this prior art ear plug requires an additional manufacturing step to secure the stem in the foam body, i.e., a gluing step. Furthermore, the bond is sometimes not as permanent as is desirable.

Figure 2:
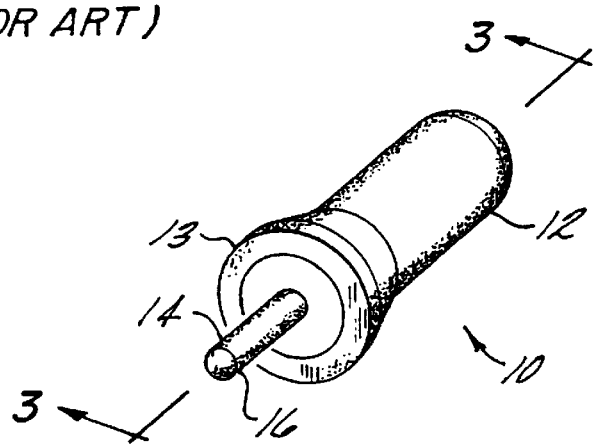
FIG. 2 is a perspective view of another prior art ear plug.
Figure 3:
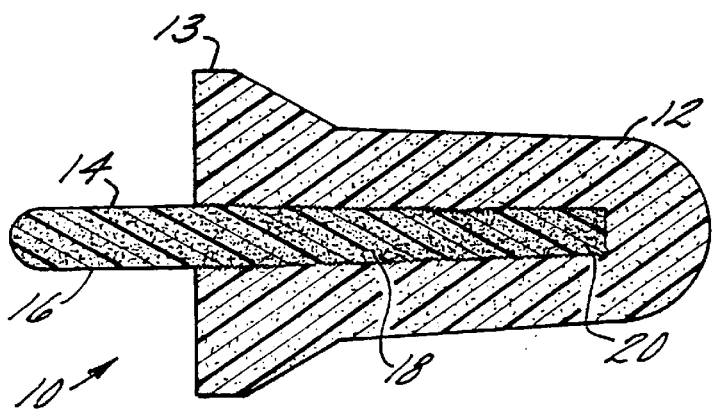
FIG. 3 is a cross-sectional view along the line 3—3 of the prior art ear plug of FIG. 2.

Referring next to FIGS. 2 and 3, another exemplary prior art device is disclosed in U.S. Pat. No. 5,799,658 to Falco which is assigned to the assignee hereof, all of the contents of which are incorporated herein by reference. This prior art earplug or semi-aural device 10 comprises a foam 12 mechanically bonded to a porous component 14 having a handle portion 16 and an embedded portion 18 with a tip 20. "Embedded portion" refers here to that part of the porous insert which is surrounded by, and mechanically bonded to, the foam component. The earplug may be of any configuration, such as circular or ovoid, with the preferred configuration having a flange 13. During manufacture, porous component 14 is placed in a mold and a foam is formed within the mold such that foam penetrates the embedded portion 18 of porous component 14, thereby forming a mechanical bond between the foam and the porous component.

One problem with the just discussed prior art ear plug is that the sources for porous component 14 are quite limited. For this and other reasons, although the above prior art ear plugs have been satisfactory for their intended purpose, there remains a need for stemmed foam ear plugs that are safe for the wearer, yet convenient and comfortable to use and which does not require a separate gluing step to adhere to the item part.

Figure 4:
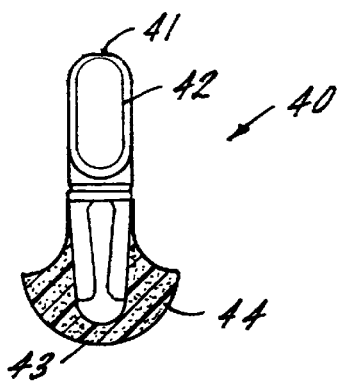
FIG. 4 is an enlarged elevational view of an ear plug in accordance with the present invention.
Figure 5:
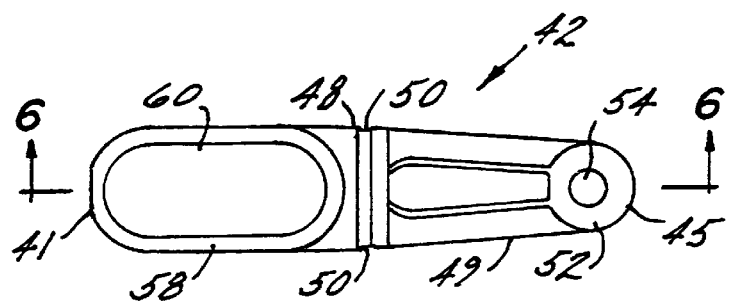
FIG. 5 is an exploded elevational view of a stem handle of the device of FIG. 4.
Figure 6:
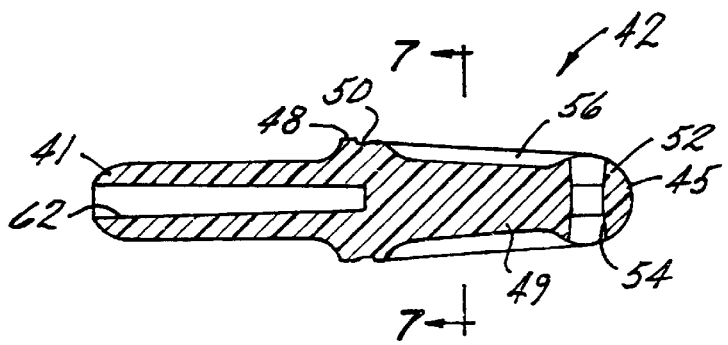
FIG. 6 is a view taken along the line 6—6 of FIG. 5

Referring now to FIGS. 4–8, a preferred embodiment of the present invention, ear plug stem (an insert component) and foam component, is shown generally at 40 (FIG. 4). Ear plug stem and foam device 40 comprises a stem 42 at a first end 41 and a foam body 44 at a second end 43. FIG. 5 is an enlarged side elevation view of the preferred embodiment of stem 42 in accordance with the present invention. FIG. 6 is a cross-sectional view taken along the line 6—6 of FIG. 5.

Stem 42 comprises an elongated member extending from first end 41 of device 40 to an opposing second end 45. In an exemplary embodiment, stem handle 42 has a length of approximately an inch and a height of approximately 0.220 inches when viewed in side elevation (see FIG. 5). Stem 42 tapers slightly toward second end 45 which is intended to be embedded in foam body 44. The tapered portion of stem 42 is generally shown at 49. Intermediate first end 41 and second end 45 is a stop shoulder 48 which is designed to stop the flow of foam 44 at stop shoulder 48 during the manufacturing process when foam 44 is injected around stem 42 to form device 40. This feature prevents wastage of foam 44 material and keeps the mold clear of flashing and the wasted time of cleaning out between cycles. Proximate stop shoulder 48 is a circumferential groove 50 which is intended to hold a retaining circle of foam adjacent stop shoulder 48.

Figure 7:
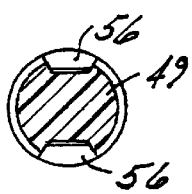
FIG. 7 is a view taken along the line 7—7 of FIG. 6.
Figure 8:
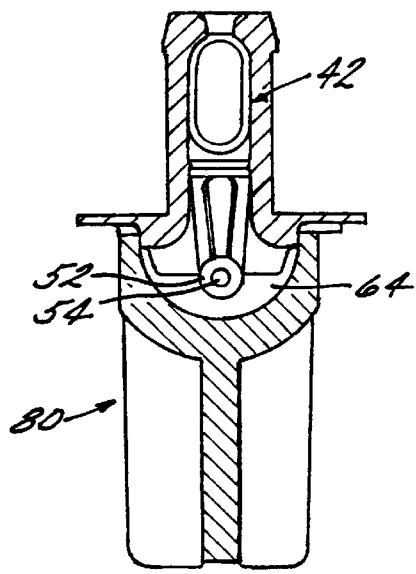
FIG. 8 is a cross-sectional view of a mold showing the stem handle of FIG. 5 in position in the mold prior to injection of the foam component for the ear plug in accordance with the present invention of FIG. 4.

Tapered portion 49 of stem 42 leading to second end 45 preferably terminates in an end member (tip portion) 52 which optionally has a width greater than tapered portion 49 of stem 42. In one exemplary embodiment, tip 52 is spherical in shape and has a diameter of 0.160 inches. It being understood that the geometric shape of tip 52 is not critical to the present invention and tip 52 may be formed of other suitable shapes which can be substituted for the sphere for tip 52. Spherical shaped tip 52 includes an opening 54 therethrough which is centrally located in spherical tip 52. In one exemplary embodiment, opening 54 has a width of about 0.062 inches. Of course, opening 54 may have any other suitable widths so long as it is not too small to permit foam body 44 from flowing therethrough during manufacture of device 40. Opening 54 is what provides the main mechanical anchor for foam body 44. Furthermore, opening 54 may be of any other shape such as square or octagonal. As best shown in FIGS. 6 and 7, stem 42 preferably includes grooves 56 formed in the tapered portion 49 of stem 42 intermediate circumferential groove 50 and tip 52. Grooves 56 can be of any desired shape and dimensions to provide additional retention surfaces for foam 44 when foam 44 is injected around stem 42.

It should be noted that the ability of device 40 to have a greater amount of foam, in turn, increases the comfort for the wearer of the ear plug. Narrowing the diameter of the cross-section of the tip 52 of the embedded portion had not been possible previously (see FIG. 1) due to the fact that the stem handle was required to be glued to the foam. An adequate bond could only be formed by gluing a larger area of the stem 42 to the foam body 44 and the adhesive itself increases the effective stem cross-section. The present invention allows formation of a stronger mechanical bond, even when using reduced stem surface area.

Stem 42 includes a stem handle portion 58 which comprises a rectangular shaped element extending from shoulder 48 in a direction away from spherical tip 52. Stem handle portion 58 has a planar shaped area 60 shown in phantom in FIG. 5 which can be advantageously utilized to display any suitable logo. Stem handle portion 58 provides an area for the user to easily grip to insert and remove ear plug device 40 from a respective ear.

FIG. 6 shows an aperture 62 which in one exemplary embodiment is preferably 0.062 in diameter and 0.496 inches deep which can hold a cord or other suitable device such as a stretchable brand (not shown) to hold two devices 40 together as a pair for retention in a person's ears. Aperture 62 is formed at first end 41 and is centrally located in stem handle 42. This cord or other suitable device is joined to the devices 40 by known means and the above-recited dimensions are recited for illustration only.

Stem 42 is fabricated by known methods and may be formed of any suitable material. Preferably, stem 42 comprises a non-porous material. Suitable materials for the stem 42 include, but are not limited to, those known in the art such as polyalkanes, polyvinylcarbonate, polypropylene, polyethylene, polyacrylates, fluoroelastomers, copolymers or multipolymers of the above, ethylene vinyl acetate, and thermoplastic elastomers, including various types of linear, diblock, triblock, and radial polymers of materials such as styrene-butadiene, isoprene-styrene, styrene-ethylene propylene and the like, and blends of the aforementioned with other materials, including metal powders. Preferred materials include polyethylene, polypropylene, ethylene-vinyl acetate, and thermoplastic elastomers, such as KRATON thermoplastic rubbers.

Suitable foams for use with the present invention include those self-rising foams suitable for use with foam ear plugs or foam components for hearing protective devices, such as earmuffs. Such foams include soft, pliable self-rising foams with instant recovery. Other foams are self-rising polyurethane or acrylic blend foams with slow recovery. One suitable foam is described in U.S. Pat. No. 5,203,352 to Gardner, herein incorporated by references. The ear plug described therein is comprised of a part slow recovery polymer and a part faster recovery polymer. Another suitable foam is described in U.S. Pat. No. 5,420,381 to Gardner, herein incorporated by reference.

In the method of manufacture of the present invention, the plastic component comprising stem 42 is placed into the cavity of an ear plug mold 80. Foam or foamable mixture is introduced into mold 80 to fill in the space between shoulder 48 and the rest of the mold cavity 64 (see FIG. 8), thus surrounding tapered second end 45 and an outside surface of spherical shaped tip 52 as well as penetrating through opening 54, thereby forming a mechanical bond between the stem handle tapered second end 45 and the finished foam body 44. The foam is introduced and expands by known means and methods. This method is particularly advantageous in that it provides a safe, useful earplug or semi-aural pod easily and efficiently, without the necessity of an additional bonding step. It has previously been very difficult to form a satisfactory bond between a stem and a foam. Furthermore, the bond formed according to the present invention is very strong, resulting in a better product. Consequently, the need for adhesives, such as glue, to bond the foam body 44 and stem handle 42 is eliminated.

A mold suitable for the practice of the method of the present invention is disclosed in U.S. Pat. No. 5,071,331 to Falco, herein incorporated by reference in its entirety. This is a known method so there is no need to discuss this method in more detail herein.

Figure 9:
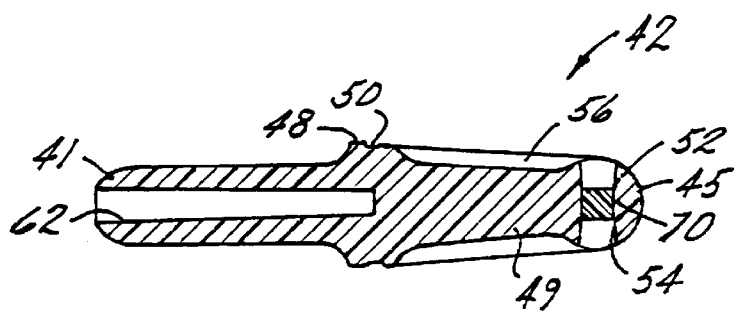
FIG. 9 is an exploded elevational view of a stem handle portion of a second embodiment of the present invention.

Turning now to FIG. 9 which illustrates a second embodiment of stem 42 in accordance with the present invention. In this embodiment, opening 54 extending through spherical shaped tip 52 does not completely extend therethrough and only partially extends through the body of spherical shaped tip 52. As illustrated, opening 54 extends inwardly through spherical shaped tip 52 from the sides; however, a wall 70 prevents opening 54 from completely extending through the body of spherical shaped tip 52. In this embodiment, the mechanical bond between foam body 44 and stem 42 results when the foam or foamable mixture is introduced into mold 80 of FIG. 8 and extends through opening 54 and abuts wall 70.

Figure 10:
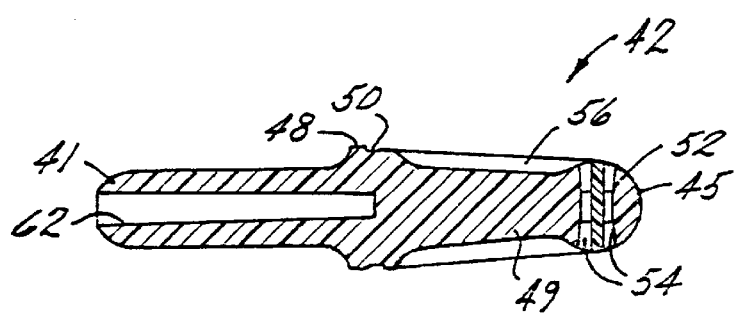
FIG. 10 is an exploded elevational view of a stem handle portion of a third embodiment of the present invention.

In yet another embodiment of the present invention illustrated in FIG. 10, spherical shaped tip 52 includes a plurality of openings 54 which extend through the body of spherical shaped tip 52 and provide multiple openings for the foam to penetrate during the molding process to create mechanical bonding between the foam body 44 and stem 42. In this embodiment, the plurality of openings 54 may completely extend through the body of spherical shaped tip 52 or may partially extend therethrough with wall 70 being present to prevent the plurality of openings 54 from extending completely through tip body 52.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A hearing protective device comprising:

a foam;

a stem initially discrete from the foam, the stem including a body having a tip at a first end, the tip having at least one opening extending through the stem body, the foam extending through the at least one opening to mechanically bond the stem to the foam.

2. The hearing protective device of claim 1, wherein the stem includes a stem handle portion opposite the tip, the tip comprising an embedded portion of the stem.

3. The hearing protective device of claim 1, wherein the stem comprises an elongated body having a stem handle portion at a second end opposite the first end and the stem body tapers slightly toward the first end.

4. The hearing protective device of claim 3, wherein the tip has a width greater than a width of the tapered portion of the stem body.

5. The hearing protective device of claim 1, wherein the tip comprises a spherical shaped end member.

6. The hearing protective device of claim 3, further including:

a stop shoulder formed in the stem body intermediate the first and second ends.

7. The hearing protective device of claim 3, wherein the stem body includes a circumferential groove intermediate the first and second ends for annularly receiving the foam to expand the mechanical bonding between the foam and the stem.

8. The hearing protective device of claim 1, wherein the stem is formed of a nonporous material.

9. The hearing protective device of claim 1, wherein the stem includes a plurality of openings formed in the tip at the first end, the plurality of openings permitting the foam to extend therethrough to mechanically bond the stem body to the foam.

10. The hearing protective device of claim 1, wherein the stem body includes at least one longitudinal groove formed therein, the longitudinal groove for receiving the foam to further mechanically retain the foam to the stem body.

11. The hearing protective device of claim 1, wherein the foam is selected from the group consisting of polyurethane, acrylic, acrylic blends, or mixtures thereof.

12. A hearing protective device, comprising:

a foam; and a stem initially discrete from the foam, the stem including a body having a tip at a first end, the tip including at least one opening which at least partially extends through the stem body, the stem being mechanically bonded to the foam by disposing the foam through the at least one opening.

13. An acoustical foam earplug or semi-aural pod with a stem, wherein the stem has a handle portion at a first end and an imbedded portion with a tip at an opposing second end, and further wherein the tip includes at least one opening extending through the tip, the stem being mechanically bonded to the foam by disposing the foam through the at least one opening.

14. The foam earplug or semi-aural pod of claim 13, wherein the stem tapers slightly toward the tip at the second end.

15. The foam earplug or semi-aural pod of claim 14, wherein the tip has a width greater than a width of the tapered portion of the stem body.

16. The foam earplug or semi-aural pod of claim 13, wherein the tip comprises a spherical shaped end member.

17. A method of making a hearing protective device comprising at least one foam component and at least one non-porous component initially discrete from the foam, the non-porous component having at least one opening extending at least partially therethrough, comprising:

placing the non-porous component into a mold;

introducing a foam or foamable mixture into the mold; and causing the foam to rise and extend through the at least one opening in the non-porous component, thereby forming a mechanical bond between the porous component and the foam.

* * * * *